US010765544B2

(12) United States Patent
Cully et al.

(10) Patent No.: US 10,765,544 B2
(45) Date of Patent: Sep. 8, 2020

(54) PUSH AND PULL MEDICAL DEVICE DELIVERY SYSTEM

(71) Applicant: W. L. Gore & Associates, Inc., Newark, DE (US)

(72) Inventors: Edward H. Cully, Flagstaff, AZ (US); Ryan D. Kariniemi, Flagstaff, AZ (US); David M. Williams, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 736 days.

(21) Appl. No.: 14/701,508

(22) Filed: Apr. 30, 2015

(65) Prior Publication Data

US 2015/0313738 A1    Nov. 5, 2015

Related U.S. Application Data

(60) Provisional application No. 61/988,038, filed on May 2, 2014.

(51) Int. Cl.
| | |
|---|---|
| *A61F 2/954* | (2013.01) |
| *A61F 2/962* | (2013.01) |
| *A61F 2/95* | (2013.01) |
| *A61F 2/92* | (2013.01) |
| *A61F 2/97* | (2013.01) |

(Continued)

(52) U.S. Cl.
CPC ........ *A61F 2/962* (2013.01); *A61B 17/00234* (2013.01); *A61B 17/3468* (2013.01); *A61F 2/2436* (2013.01); *A61F 2/92* (2013.01); *A61F 2/95* (2013.01); *A61F 2/966* (2013.01); *A61F 2/97* (2013.01); *A61B 17/3415* (2013.01); *A61F 2/07* (2013.01); *A61F 2/954* (2013.01); *A61F 2002/823* (2013.01); *A61F 2002/9522* (2013.01); *A61F 2220/0033* (2013.01);
(Continued)

(58) Field of Classification Search
CPC ...... A61F 2/962; A61F 2/97; A61B 17/00234; A61B 17/3468
USPC ................ 623/1.11, 1.12; 606/108, 194, 195
See application file for complete search history.

(56) References Cited

U.S. PATENT DOCUMENTS

| | | |
|---|---|---|
| 5,591,228 A | 1/1997 | Edoga |
| 6,042,605 A | 3/2000 | Martin et al. |

(Continued)

FOREIGN PATENT DOCUMENTS

WO    99/18889    4/1999

OTHER PUBLICATIONS

International Search Report and Written Opinion for PCT/US2015/028903 dated Aug. 18, 2015, corresponding to U.S. Appl. No. 14/701,508, 6 pages.

*Primary Examiner* — Vy Q Bui

(57) ABSTRACT

A system for delivery of a medical device includes a delivery member and a medical device, which is mounted to the delivery member and releasably retained in a delivery configuration for endoluminal delivery of the medical device toward a treatment site in a human vessel. The delivery member includes an elongated first portion configured to extend outside of the body from a first percutaneous access site and an elongated second portion configured to extend outside the body from a second percutaneous access site to allow positioning of the medical device at the treatment site by manipulation of the first portion and second portion from outside of the body.

31 Claims, 17 Drawing Sheets

(51) Int. Cl.

| | | |
|---|---|---|
| | *A61F 2/966* | (2013.01) |
| | *A61F 2/24* | (2006.01) |
| | *A61B 17/34* | (2006.01) |
| | *A61B 17/00* | (2006.01) |
| | *A61F 2/82* | (2013.01) |
| | *A61F 2/07* | (2013.01) |

(52) U.S. Cl.
CPC ............... *A61F 2220/0075* (2013.01); *A61F 2250/0019* (2013.01); *A61F 2250/0029* (2013.01)

(56) References Cited

U.S. PATENT DOCUMENTS

| | | | |
|---|---|---|---|
| 6,352,561 B1 | 3/2002 | Leopold et al. | |
| 6,626,939 B1* | 9/2003 | Burnside | A61F 2/07 623/1.38 |
| 6,849,087 B1 | 2/2005 | Chuter | |
| 6,899,727 B2* | 5/2005 | Armstrong | A61F 2/95 623/1.12 |
| 8,128,680 B2* | 3/2012 | De La Menardiere | A61F 2/954 623/1.23 |
| 9,669,191 B2* | 6/2017 | Chou | A61F 2/958 |
| 2007/0167955 A1 | 7/2007 | Arnault et al. | |
| 2011/0213459 A1 | 9/2011 | Garrison et al. | |
| 2013/0046371 A1* | 2/2013 | Greenberg | A61F 2/95 623/1.11 |
| 2015/0351943 A1* | 12/2015 | Shalev | A61F 2/07 623/1.12 |

* cited by examiner

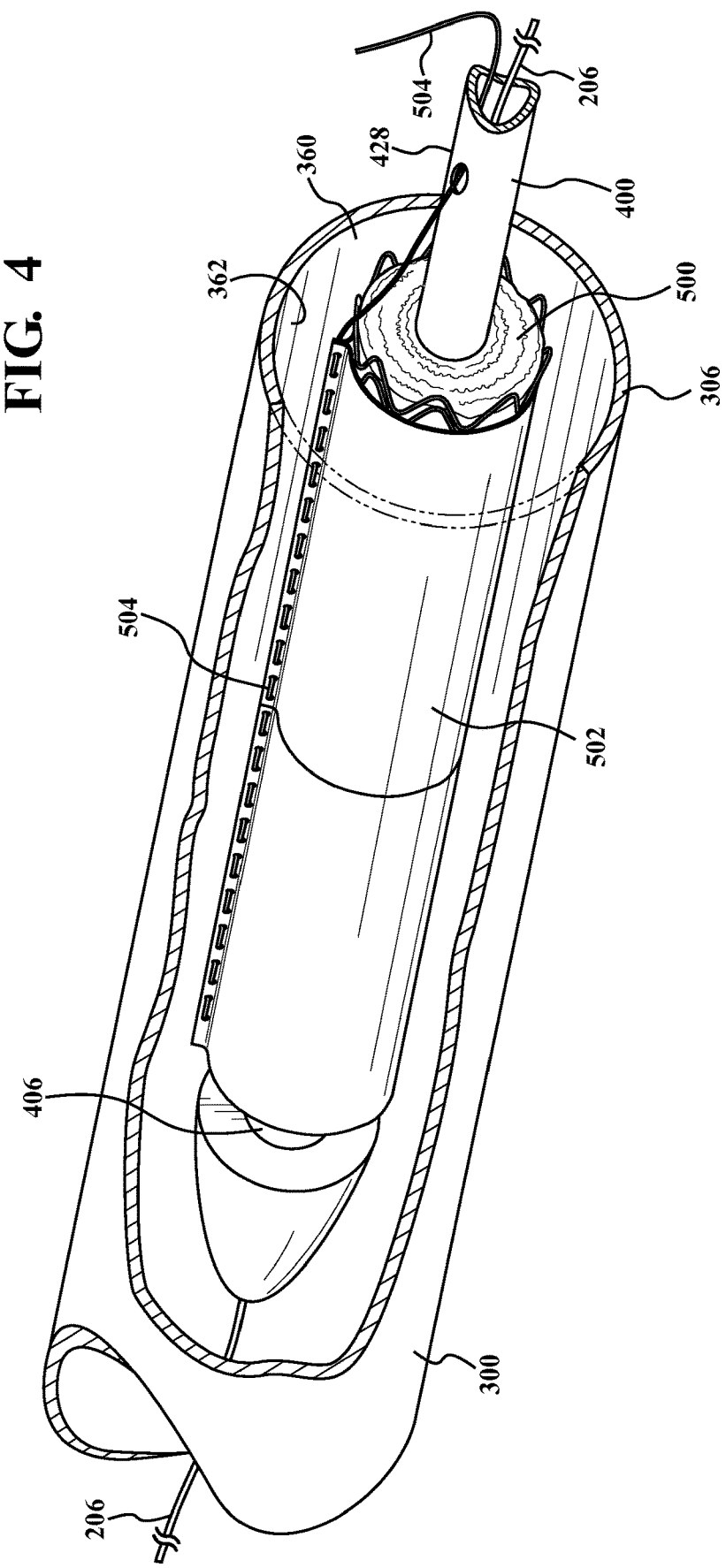

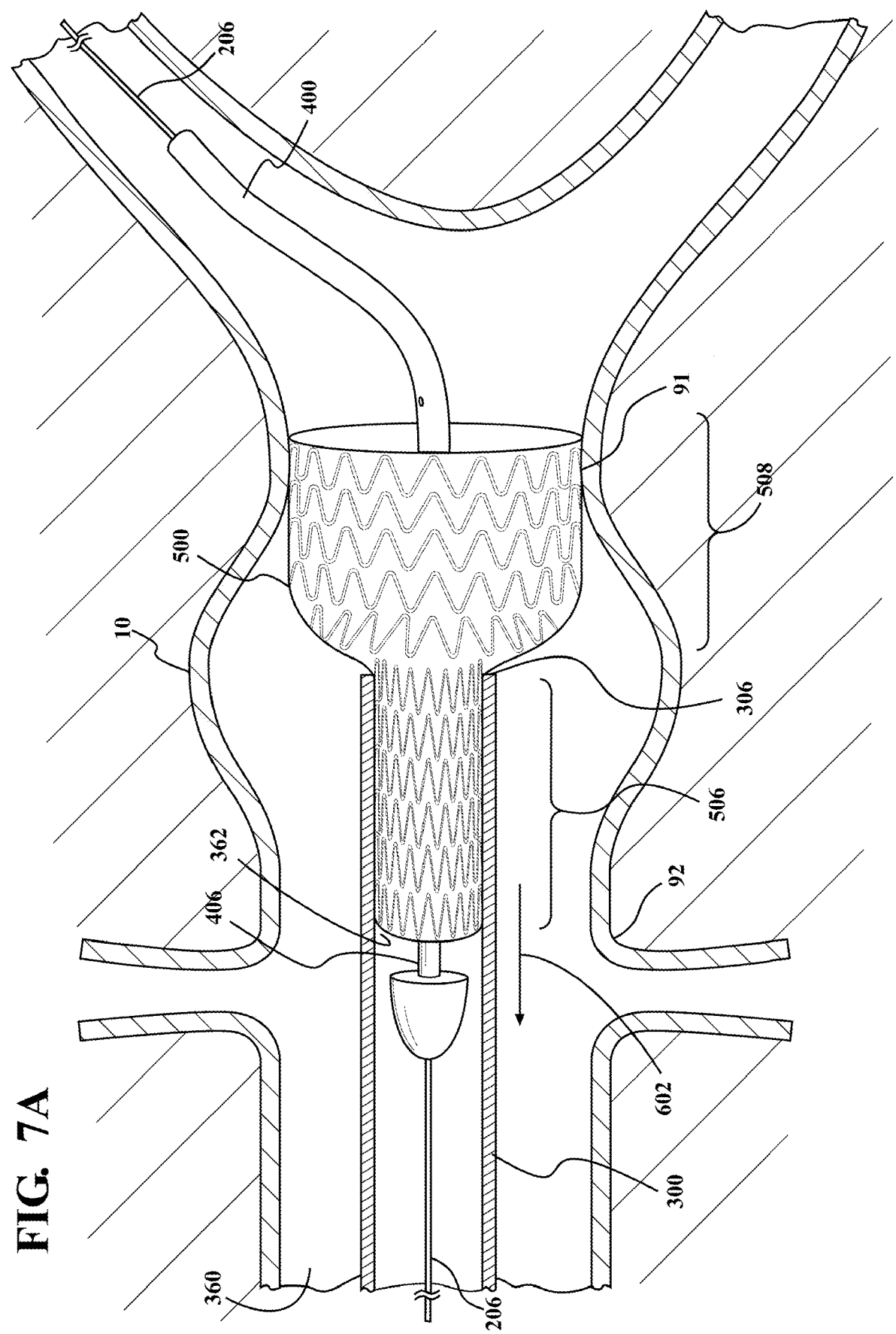

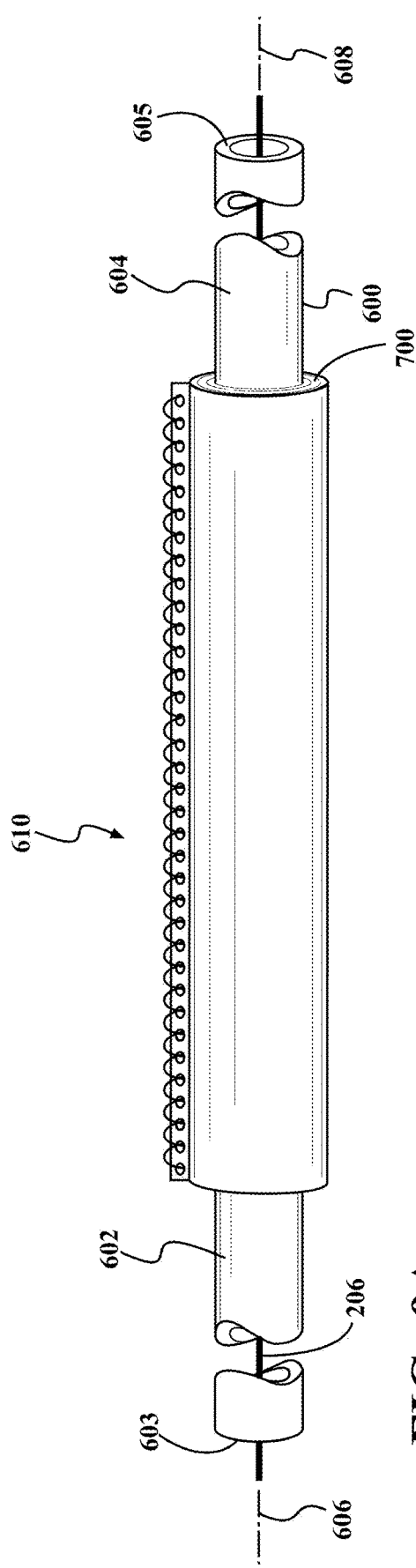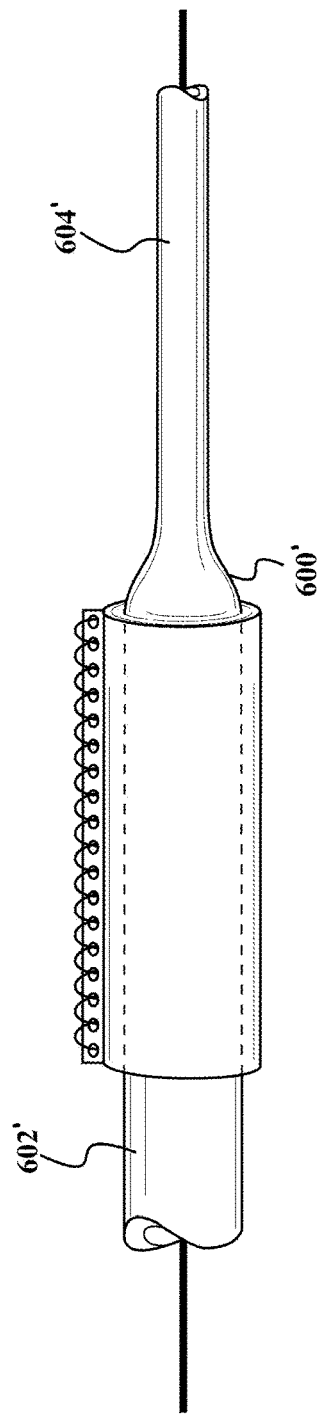
FIG. 9A
FIG. 9B

PUSH AND PULL MEDICAL DEVICE DELIVERY SYSTEM

BACKGROUND

Field

The present disclosure relates to delivery systems for implantable medical devices and, more particularly, relates to delivery systems for endoluminal delivery and push-pull positioning of implantable medical devices utilizing multiple percutaneous access points.

Discussion of the Related Art

The use of implantable medical devices in the treatment of diseased vasculature and other body conduits has become commonplace in the medical field. Such devices can be surgically implanted in or delivered endoluminally to the treatment site. In the latter case, these devices are typically retained in a compacted crown diameter along a leading end of a catheter for insertion through a percutaneous access site. It can be desirable for the catheter to have sufficient rigidity to enable a clinician to push the catheter through the single access point and traverses the vasculature without bunching or buckling and further allow axial or rotational control while positioning the device at the treatment site. On the other hand, it is at times desirable for the catheter to have sufficient flexibility to traverse tortuous vasculature. In some cases, multiple access sites and/or multiple catheters can be used to deliver multiple devices and/or related tools to the treatment site. Multiple access sites and catheters may help the healthcare provider to accomplish more complicated procedures, but current multiple access site delivery schemes still have some weaknesses in delivering medical devices accurately.

Multiple percutaneous access sites may be useful in the aorta wherein one access is radial or brachial and the other is iliac or femoral. In the peripheral anatomy, a clinician may use a pedal access along with iliac or femoral to place a device such as stent, stent-graft or use and control endovascular tools such as embolectomy, CTO, Thrombectomy or atherectomy tools. Other potential access sites include translumbar access to the aorta, transapical access in the heart to radial, brachial or femoral, femoral to femoral over the aortic bifurcation, any venous access, crossing the atrial septum and continuing on to any appropriate arterial access site. As has become obvious, any multiple access sites may be envisioned which, when traversed by an endoluminal tool, can provide a clinician enhanced peri-procedural control of endoluminal tools and devices. Likewise, the access and egress should not be limited to the vascular system. These same benefits apply to other bodily systems such as gastrointestinal, colo-rectal, esophageal and biliary. It is also envisioned there is benefit in procedures such as bypass grafting wherein the tools and devices actually leave the host lumen path and establish an alternate route and even wherein there is no host vessel at all, such as in placement of indwelling electrical leads for neurostimulation or similar.

Therefore, it remains desirable to provide a multiple access site delivery system that facilitates accurate and efficient endoluminal deployment of implantable devices and endovascular tools.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

FIG. 4 shows a schematic representation of a device on a second catheter and the second catheter inside a first catheter prior to at least a partial transfer of the device from the second catheter to the first catheter.

FIG. 7A shows a schematic of human anatomy with a device partially deployed from a second catheter to a vessel wall on one end of the device and constrained by a first catheter on an opposite end of the device and the device expanding against a vessel.

FIG. 9A shows a device constrained along a catheter.

FIG. 9B shows a catheter with a first larger outer diameter, and a device constrained along the first larger outer diameter, and a second outer diameter less than the first outer diameter.

DETAILED DESCRIPTION

Figure 1:
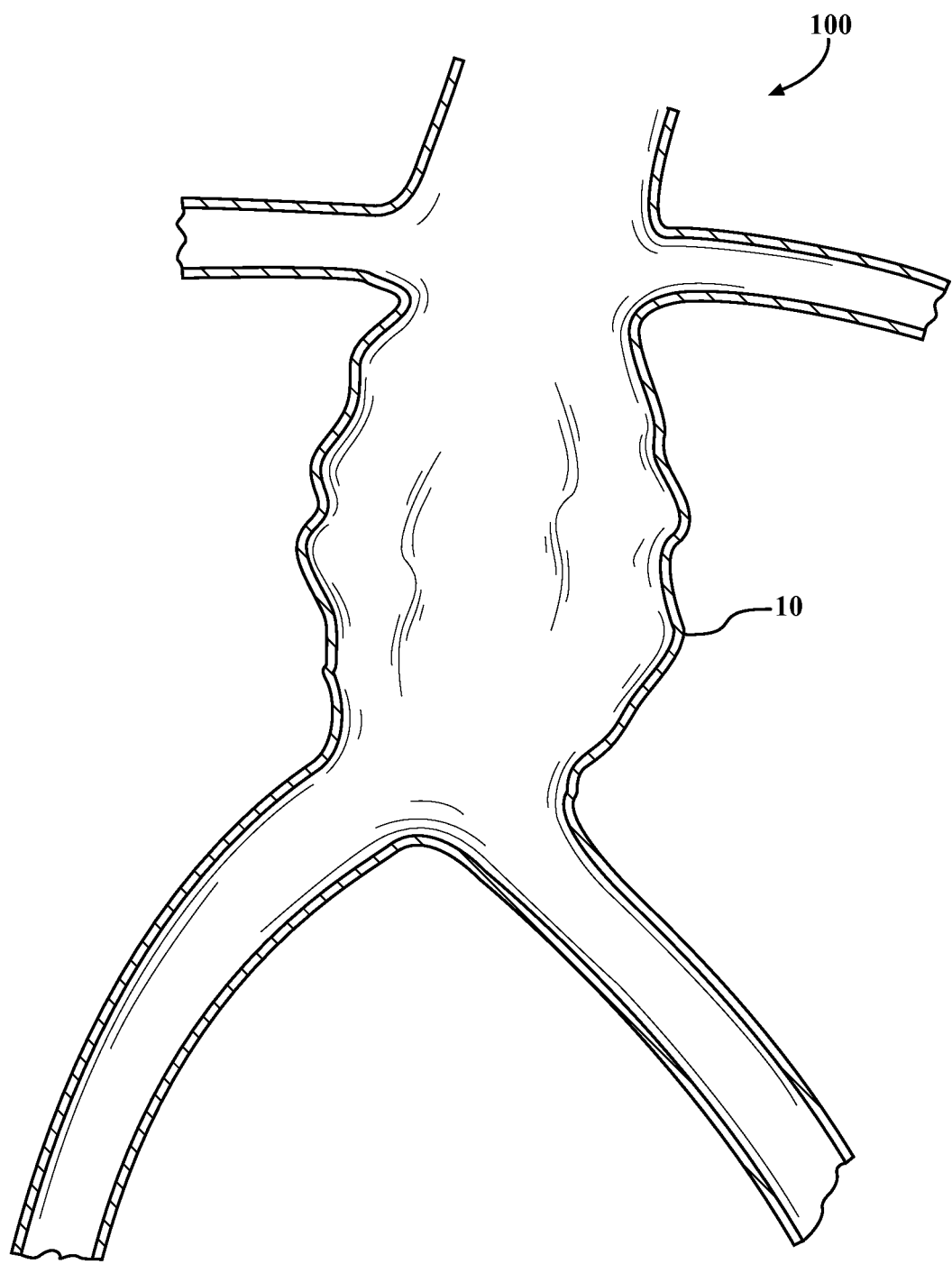
FIG. 1 shows a schematic representation of human anatomy from the aortic valve to the iliac vessels.
Figure 2:
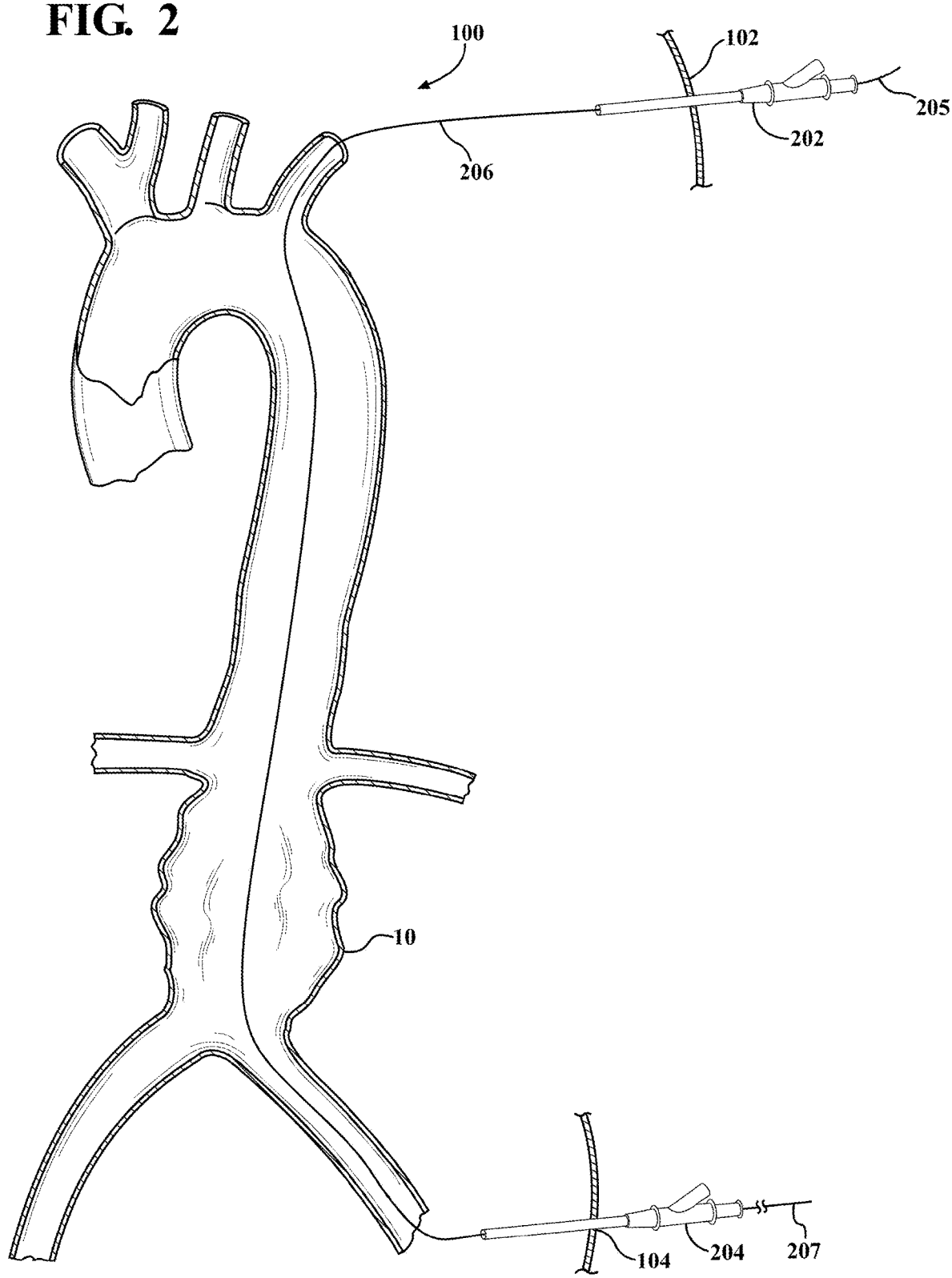
FIG. 2 shows a schematic of the human anatomy and the placement of a guidewire and introducer sheath into the human anatomy.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

Delivery systems for deployment of expandable devices or implants are disclosed herein which utilize multiple percutaneous access sites for treating a variety of vascular diseases, as shown in FIG. 1, for example, for treating aneurysms 10 along a vessel 100, Although illustrated in the context of deploying a stent graft for treatment of an abdominal aortic aneurysm (AAA), it should be appreciated that the devices, systems and methods described herein are not limited to treatment of AAA's and can be applied to delivery of any endoluminally deliverable device, component or tool for treatment of disease in other parts of human vasculature. Examples of stent grafts usable with delivery systems in accordance with the present disclosure are disclosed in U.S. Pat. No. 6,042,605 to Martin et. al.

Referring to FIGS. 2, 3A, 3B and 3C, a delivery system is shown in a configuration utilizing two or more percutaneous access sites 102, 104. In this configuration, the delivery system allows push-pull positioning and delivery of an expandable device at a vascular treatment site through manipulation of at least two portions or members of the delivery system from outside of the body from respective access sites. The delivery system can include first and second introducer sheaths 202, 204 to facilitate introduction of surgical implements through respective access sites 102, 104. The delivery system includes a guidewire 206 that can be routed through a portion of vasculature to be treated in a "body floss" or "through-and-through" access configuration, wherein opposite terminal ends 205, 207 of the guidewire 206 extend outside of the body from respective percutaneous access sites 102, 104 via the first and second introducer sheaths 202, 204.

Figure 3A:
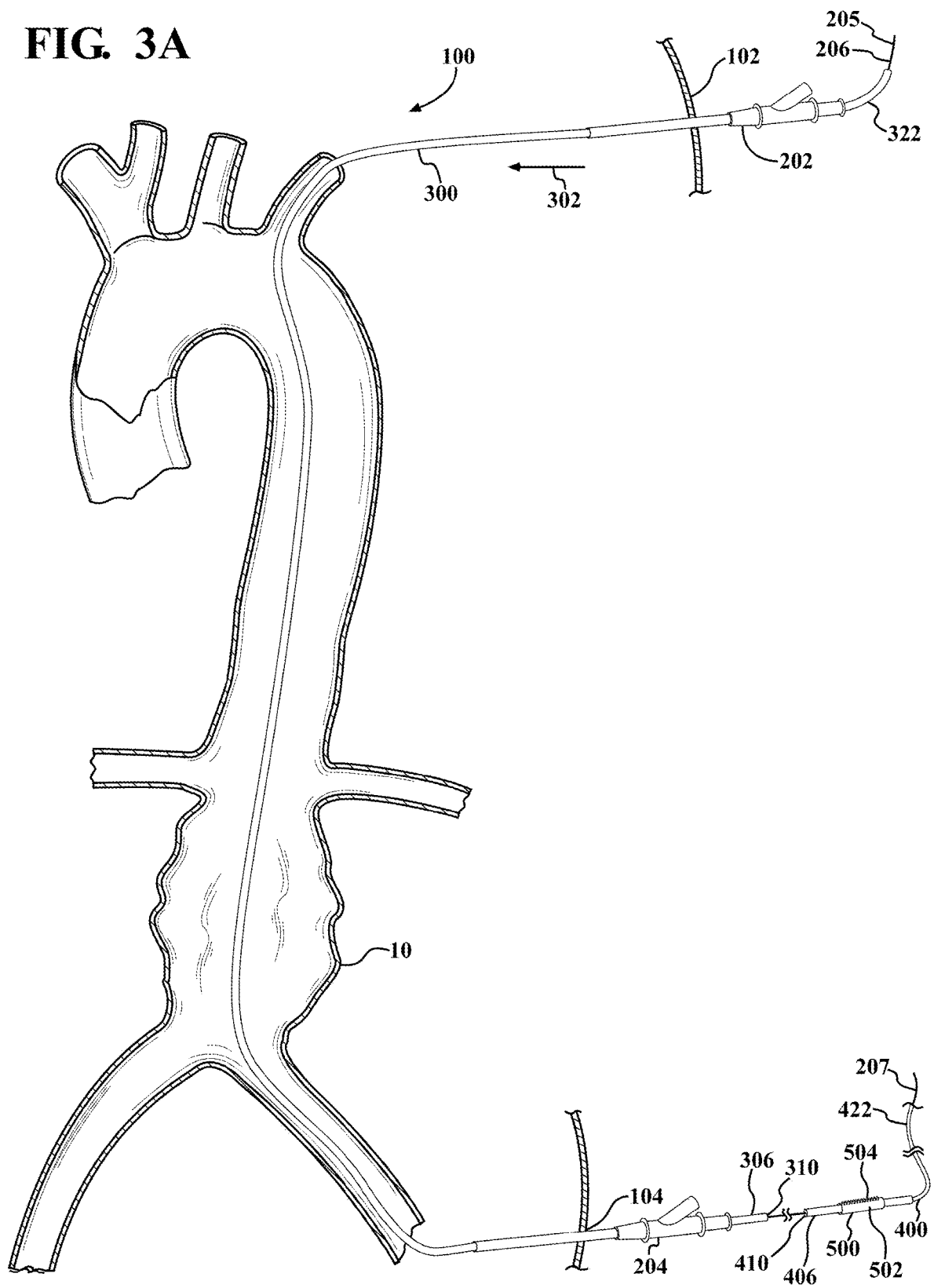
FIG. 3A shows a schematic representation of human anatomy with a first catheter fed through a first access site and out a second access site.

A delivery system for endoluminal delivery of an implantable medical device can include elongated first and second catheters extending through respective first and second percutaneous access points and releasably coupled to each other at leading ends thereof to allow a push-pull or a pull-pull positioning of the implantable medical device prior to full deployment at the treatment site. For example, as shown in FIG. 3A, a first catheter, generally indicated at 300, includes a leading end 306 and an opposite trailing end 322. The first catheter 300 has a guidewire lumen 310 through which a guidewire 206 can be routed. A first end 205 of the guidewire 206 can be inserted into the guidewire lumen 310 at the leading end 306 of the first catheter 300. The leading end 306 of the first catheter 300 can be fed into the vasculature through the first access site 102 via the first introducer sheath 202. The first catheter 300 can then be pushed along the guidewire 206 in the direction indicated at 302 until the leading end 306 exits the second access site 104. The trailing end 322 of the first catheter 300 remains outside of the body and extends from the first access site 102 via the first introducer sheath 202. In this configuration, the catheter 300 can be maneuvered by pushing or pulling the leading end 306 and trailing ends 322 of the first catheter 300 from outside of the body.

Alternatively, the catheter 300 can be inserted through the second access site 104 via the second introducer sheath 204, translated in a retrograde direction opposite the direction indicated at 302, and out of the first access site 102. In either case, transfer of the leading end 306 between the first access site 102 and second access site 104 can be facilitated with a snare. This can be helpful if the catheter has a low bending or column strength such that it can not be effectively navigated between access sites by only pushing on one end of the catheter from outside the body.

Still referring to FIG. 3A, a second catheter, generally indicated at 400, includes a leading end 406 and an opposite trailing end 422. The second catheter 400 has a guidewire lumen 410 for receiving the guidewire 206 therethrough. The second end 207 of the guidewire 206 can be inserted into the guidewire lumen 410 at the leading end 406 of the second catheter 400. The second catheter 400 can be pushed along the guidewire 206 until the leading ends 306, 406 engage.

An expandable device can be releasably coupled to one of the first and second catheters at or near the leading end thereof. The expandable device can be releasably maintained or radially compressed toward a delivery configuration for endoluminal delivery by any suitable constraining means, such as a film constraining sleeve, a constraining tether or lattice, retractable sheath and the like. For example, as illustrated in FIG. 3A, an expandable device 500 is disposed at or near the leading end 406 of the second catheter 400. The expandable device 500 is compressed and held toward the delivery configuration by a constraining sleeve 502 extending about the expandable device 500 and having opposite ends or portions held together by a release line 504. The release line 504 can be disengaged from the constraining sleeve 502 to allow the device 500 to expand radially outwardly toward an unconstrained state or a partially unconstrained state or otherwise toward engagement with surrounding vessel walls at the treatment site. Optionally, one or more constraining means or combination of constraining means can be configured to allow staged expansion through one or more intermediate expanded states prior to full deployment. An example of means for releasably constraining a device for endoluminal delivery is provided in U.S. Pat. No. 6,352,561 to Leopold et al.

Figure 3B:
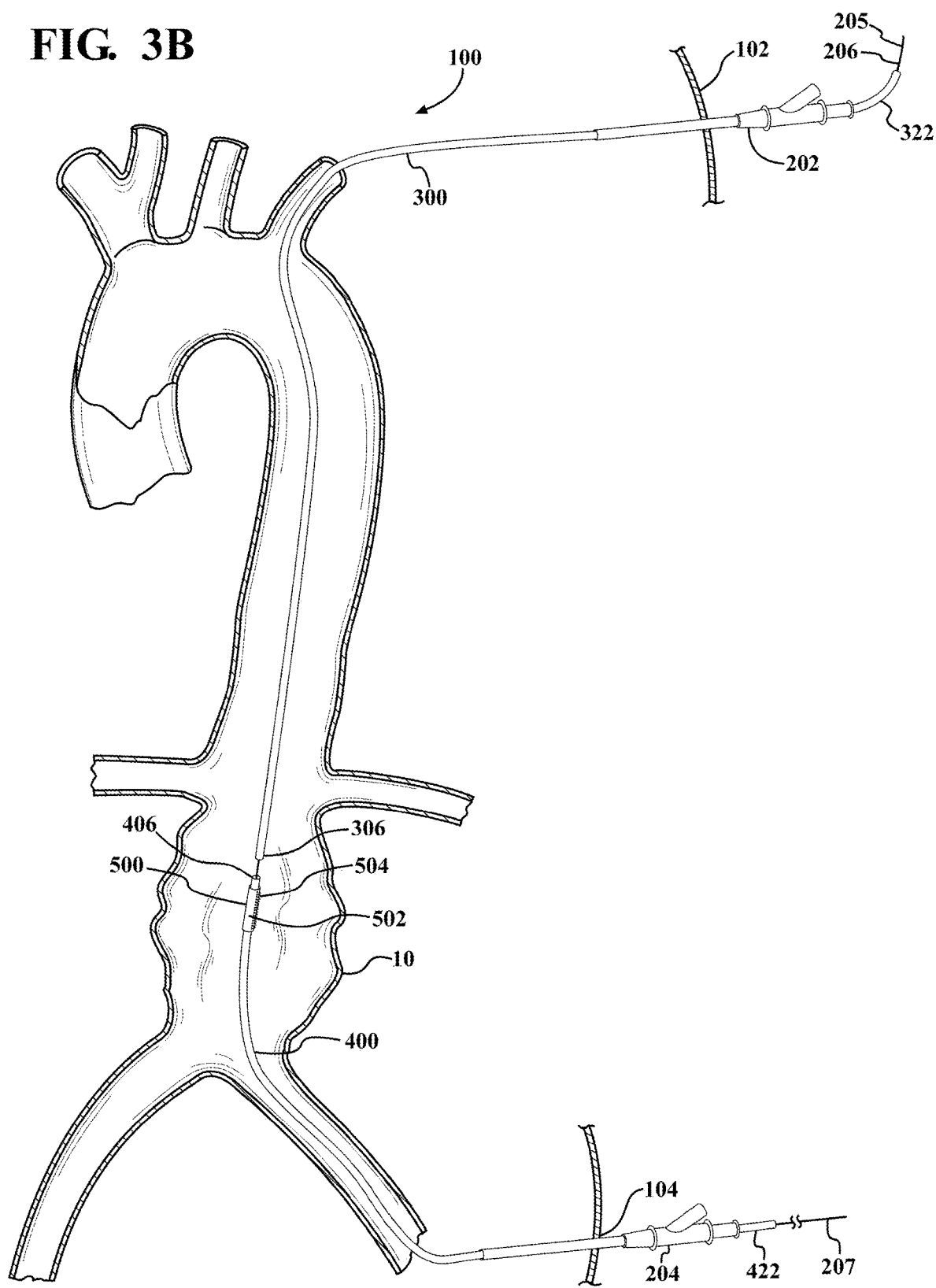
FIG. 3B shows a schematic representation of human anatomy with a first catheter protruding from a first access site and a second catheter protruding from a second access site with a constrained device on the second catheter insitu.

The leading ends 306, 406 of the first and second catheters 300, 400 can be configured for matingly engaging or coupling to each other. Further, the leading ends 306, 406 can be configured for releasably coupling to each other. Coupling of the leading ends can be achieved by a variety of coupling arrangements. Non-limiting examples of coupling arrangements can include press fitting, threads, ball and detent, articulating clips or jaws, hook and loop, and magnetic. The leading ends 306, 406 of the first and second catheters 300, 400 can be coupled to each other extracorporeal, as shown in FIG. 3A. Alternatively, the first and second catheters 300, 400 can be inserted into respective first and second access sites 102, 104 and the leading ends 306, 406 can be coupled in situ at or around the treatment site, as shown in FIG. 3B.

Figure 8:
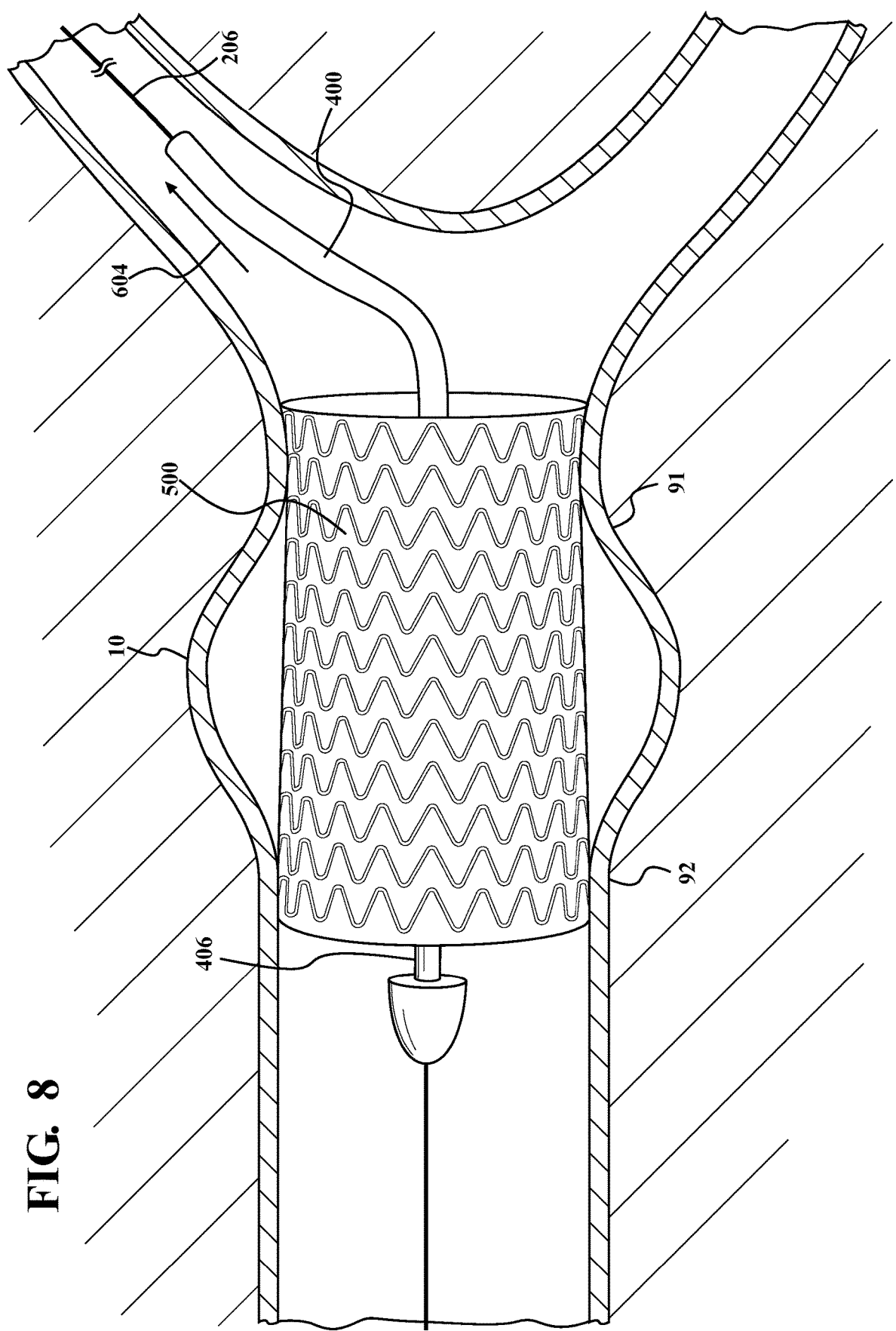
FIG. 8 shows a schematic of human anatomy with a device deployed from a second catheter and expanded against a vessel.

Once the leading ends 306, 406 are coupled, trailing ends 322, 422 of the first and second catheters 300, 400 outside of the body can be pushed, pulled and rotated to axially and rotatably position the expandable device 500 at the treatment site. After the expandable device 500 has been positioned at a desirable location and orientation at the treatment site, the expandable device 500 can be fully deployed to engage the surrounding vessel walls at the treatment site, as shown in FIG. 8.

Leading ends of first and second catheters can be coupled by providing an expandable device in a delivery configuration on a leading end of one of the first and second catheters and partially deploying the expandable device toward releasable engagement with a leading end of the other of the first and second catheters. The implantable prosthesis can be at least partially constrained along an outer wall of one of the first and second catheters and at least partially constrained along an inner wall of one of the first and second catheters, thereby forming a releasable connection between the first and second catheters. As shown in FIG. 4, for example, an expandable device 500 is disposed at or near the leading end 406 of the second catheter 400. More specifically, at least a portion of the expandable device 500 extends along an outer surface 428 of the second catheter 400 at or near the leading end 406 of the second catheter 400. The expandable device 500 is compressed and held toward the delivery configuration by a constraining sleeve 502 held together by a release line 504. The release line 504 can be disengaged from the constraining sleeve 502 to allow at least a portion of the device 500 to expand radially outwardly toward engagement with the leading end 306 of the first catheter 300. In a number of embodiments, the leading end 306 of the first catheter 300 can include a bore 360 defined by an inner surface 362. The inner surface 362 can be generally annular for receiving therein the leading end 406 of the second catheter 400 and the constrained expandable device 500 supported thereon.

Figure 5:
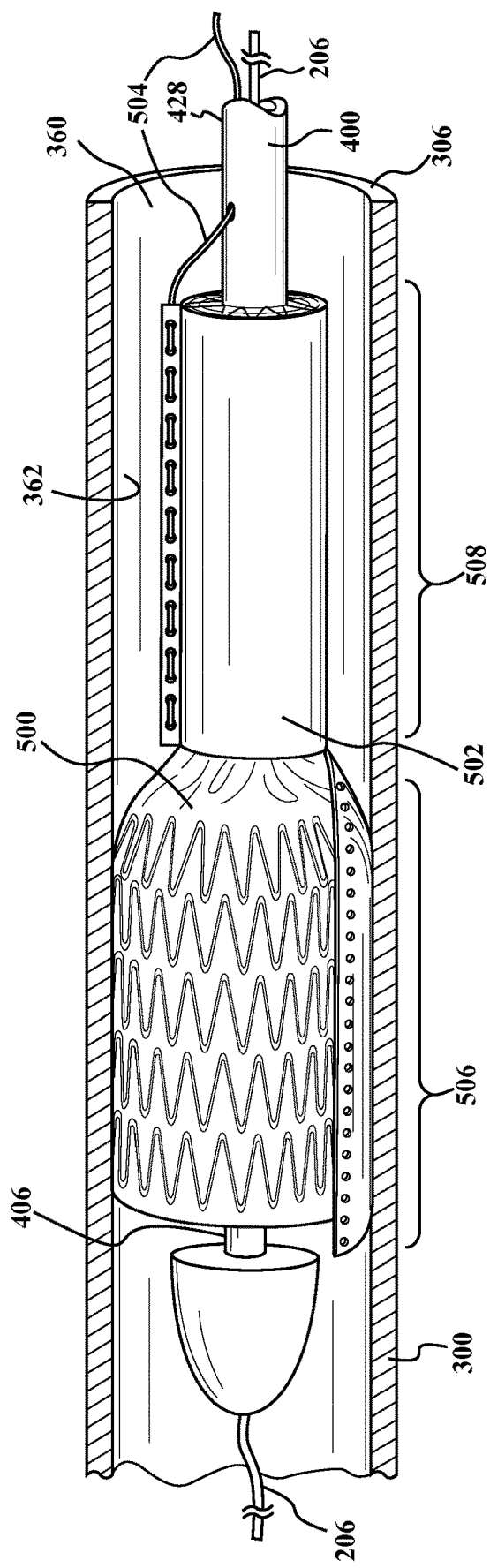
FIG. 5 shows a side view of a device on a second catheter partially deployed along a first catheter.
Figure 6:
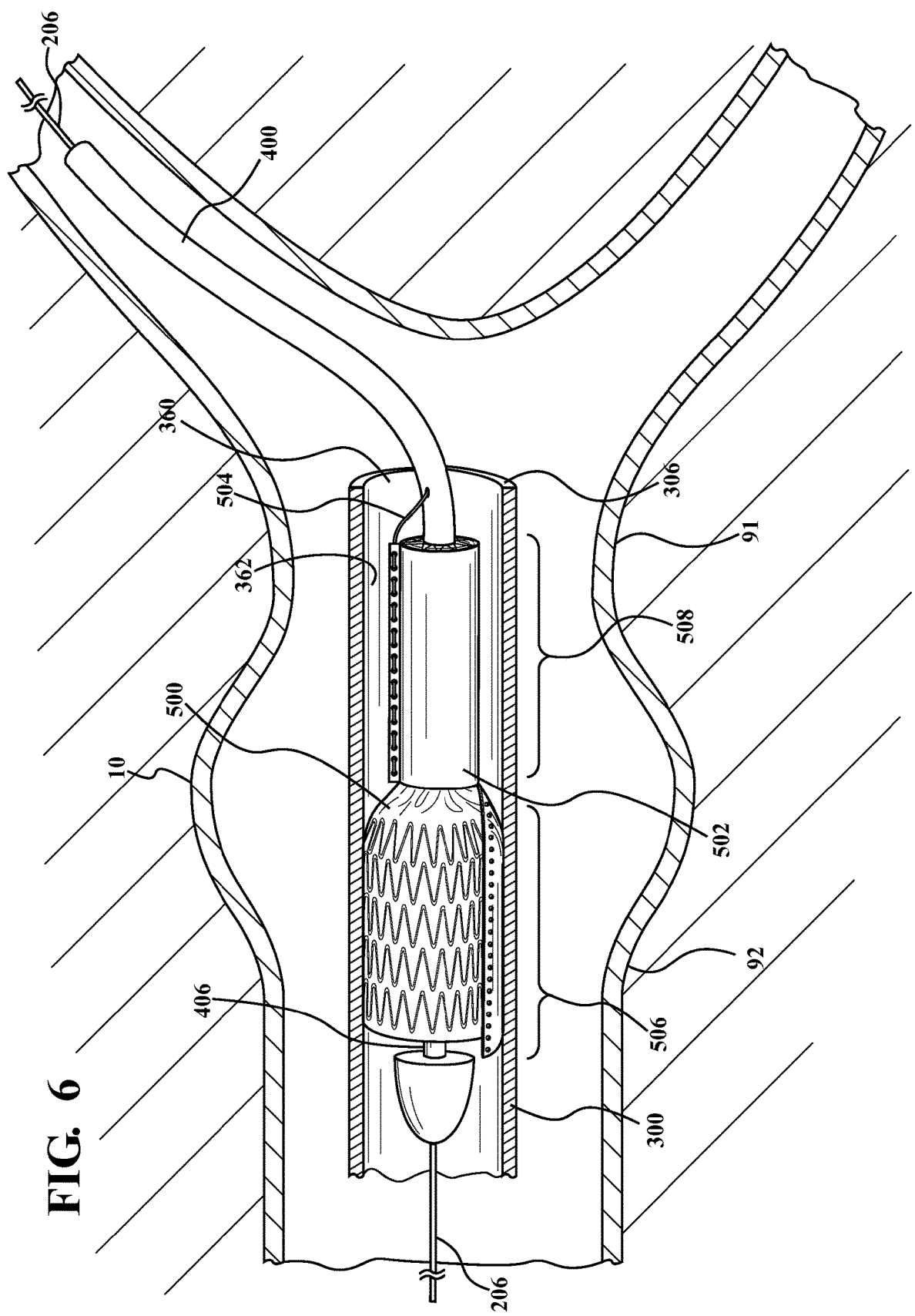
FIG. 6 shows a schematic of human anatomy with a device on a second catheter partially deployed along a first catheter.

Referring to FIG. 5, disengagement of the release line 504 from the constraining sleeve 502 allows at least a portion of the device 500 to expand radially outward toward engagement with the inner surface 362 at the leading end 306 of the first catheter 300. A partially expanded portion 506 of the expandable device 500 has an engagement length measured by the length of the partially expanded portion 506 engaged with the inner surface 362 to create a releasable interconnection between the first and second catheters 300, 400. A remaining constrained portion 508 of the expandable device 500 may at least partially extend in the leading end 306 of the first catheter 300. The partially expanded portion 506 should apply sufficient outward radial force against the inner surface 362 to form a frictional coupling between the first and second catheters 300, 400 that allows, in one configuration, the first and second catheters 300, 400 to be pushed and/or pulled and/or rotated to axially and/or rotatably position the expandable device 500 at the treatment site. In another configuration, the coupling formed by the engagement between the partially expanded portion 506 and the inner surface 362 is releasable to allow decoupling and separation of the first and second catheters 300, 400.

An opened section of the constraining sleeve 502 along the partially expanded portion 506 can be configured to remain between the first catheter inner wall and the expandable device 500. Alternatively, the constraining sleeve or portions thereof can be configured to be completely removed after deployment of the expandable device at the treatment site.

Optionally, the inner surface 362 can be configured to enhance the engagement or coupling between the first catheter 300 and second catheter 400. For example, the inner surface 362 can include a texture or a rubber-like coating or layer to increase friction between the expandable device and the inner surface. Alternatively, the inner surface 362 can have cross-sectional profile that corresponds with or otherwise forms an interference engagement with an outer profile of the expandable device 500.

Once the leading ends 306, 406 are coupled, trailing ends 322, 422 of the first and second catheters 300, 400 outside of the body can be pushed, pulled and rotated to axially and rotatably position the expandable device 500 at the treatment site. After the expandable device 500 has been positioned at a desirable location and orientation at the treatment site, the expandable device 500 can be fully deployed to engage the surrounding vessel walls at the treatment site, as shown in FIG. 8.

In one deployment mode, the constraining sleeve 502 can be opened by displacing the release line 504 from the constraining sleeve 502 to allow the remaining constrained portion 508 to expand toward engagement with surrounding vessel walls on a first side 91 of an aneurysm 10 at the treatment side, as shown in FIG. 7A. With the expandable device 500 still releasably coupled to the second catheter 400 and/or with the device 500 engaged with engaged or anchored with the vessel walls, the first catheter 300 can be displaced proximally or away from the second catheter 400, as indicated at arrow 602, to overcome the frictional engagement between the expandable device 500 and the inner surface 362. The displacement of the first catheter 300 away from the second catheter 400 allows the partially expanded portion 506 of the expandable device 500 to expand toward engagement with surrounding vessel walls on a second side 92 of the aneurysm 10, thereby completing exclusion of the aneurysm 10 from normal blood flow through the vessel, as shown in FIG. 8.

Figure 7B:
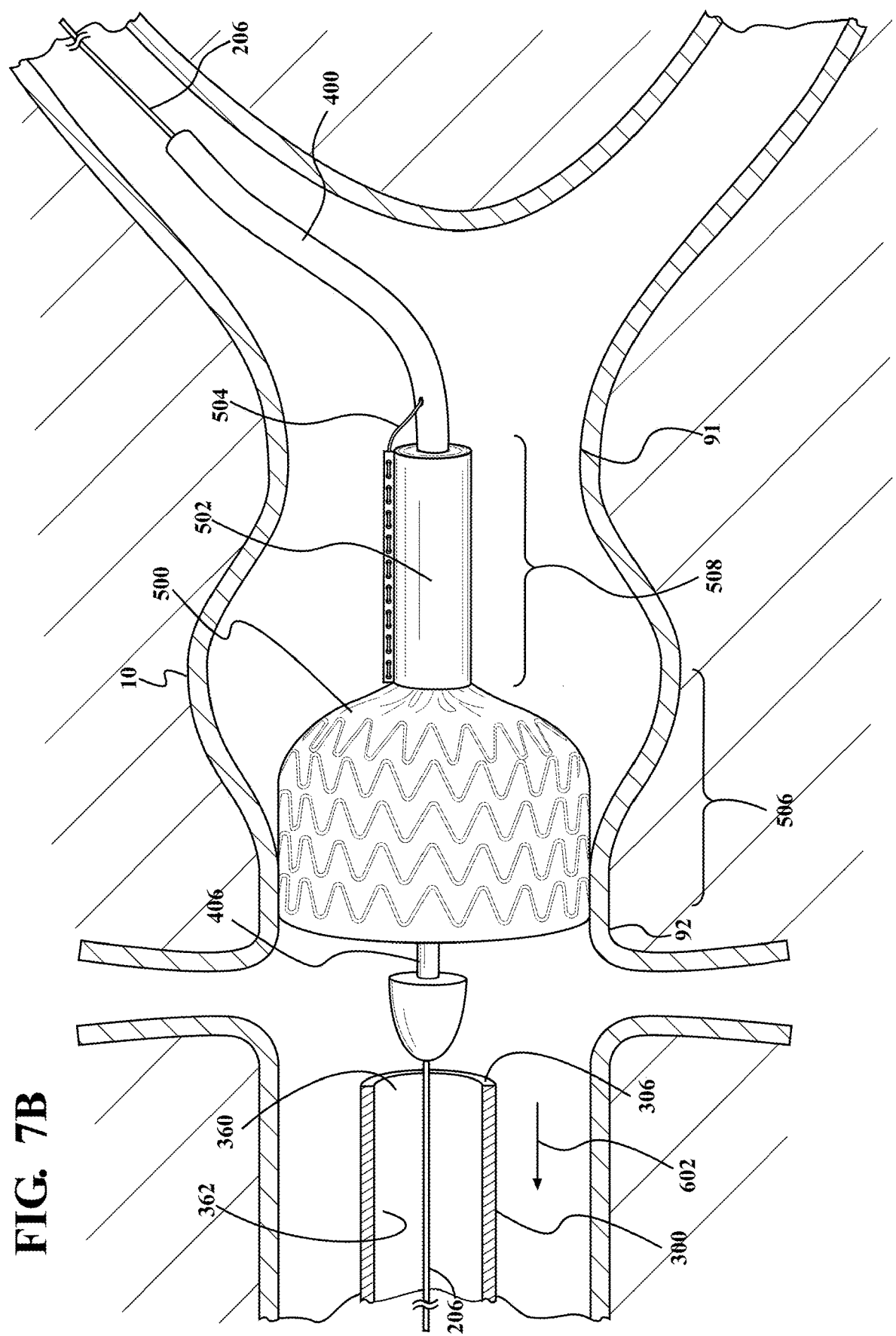
FIG. 7B shows a schematic of human anatomy with a device partially constrained along a second catheter on one end of the device and partially deployed from a first catheter and expanded against a vessel on an opposite end of the device.

In an alternate deployment mode, the first catheter 300 can be displaced proximally or away from the second catheter 400, as indicated at arrow 602, to overcome the releasable connection between the first and second catheters 300, 400 due to the frictional engagement between the expandable device 500 and the inner surface 362. The displacement of the first catheter 300 away from the second catheter 400 allows the partially expanded portion 506 of the expandable device 500 to expand toward engagement with surrounding vessel walls on the second side a2 of the aneurysm 10, as shown in FIG. 7B. The remaining constrained portion 508 of the expandable device 500 can be allowed to expand toward engagement with the surrounding vessel walls at the treatment site by displacing the release line 504 from the constraining sleeve 502, thereby completing exclusion of the aneurysm from normal blood flow through the vessel, as shown in FIG. 8.

Following deployment of the expandable device 500, the first and second catheters 300, 400 can be removed from the treatment site and body from respective treatment sites (not shown).

Alternatively, at least one of the first and second catheters of the delivery system can be substantially more flexible than the other of the first and second catheters to facilitate traversing tortuous anatomy. For example, a first catheter can be chosen to be a Pebax material with an outer diameter of 0.5 inches and an inner diameter of 0.040 inches with a durometer of X. A second catheter can be chosen to be a Pebax material with an outer diameter of 0.2 inches and an inner diameter of 0.040 inches with a durometer of 0.45×. Other parameters can be varied to achieve different ratios of one catheter to the other. For example, the outer and inner diameters can be changed, a reinforcing member can be added to one or both of the catheters, or other suitable materials can be chosen.

Alternatively, one or both of the first and second catheters can have substantially no column strength or at least can be flexible so as to not be effectively pushable into and through the vasculature. A potential advantage of having a catheter with substantially no column strength is the catheter can be more easily fed through a vessel (e.g. pushed by blood in an antegrade fashion or pulled by a snare through tortuous anatomy). For example, a first catheter can comprise a Pebax material with an outer diameter of about 8 mm and an inner diameter of about 1.1 mm with a durometer of X. A second catheter can comprise a Pebax material with an outer diameter of approximately 4 mm and an inner diameter of about 1.1 mm with a durometer of about 0.5×. In another example, the second catheter can be an ePTFE tubular structure with desired outer and inner diameters. One such example of making an ePTFE tubular structure of approximately 8 mm inner diameter and 8.14 mm outer diameter is described below. Wrap a 80 cm long by 40 mm wide by 0.03 mm thick and approximately 0.3 g/cc density of porous expanded PTFE film with an adhesive on one side of the expanded PTFE film about an 8 mm diameter cylindrical stainless steel mandrel with the adhesive facing out and at least overlap the first layer longitudinal seam at least once, and then trim the excess film and heat the film-wrapped mandrel. The density of non-porous PTFE is about 2.2 g/cc; consequently, this film is about 86% porous.

Optionally, one or both of the first and second catheters can be tapered to facilitate entry into and movement through the vasculature.

Figure 9C:
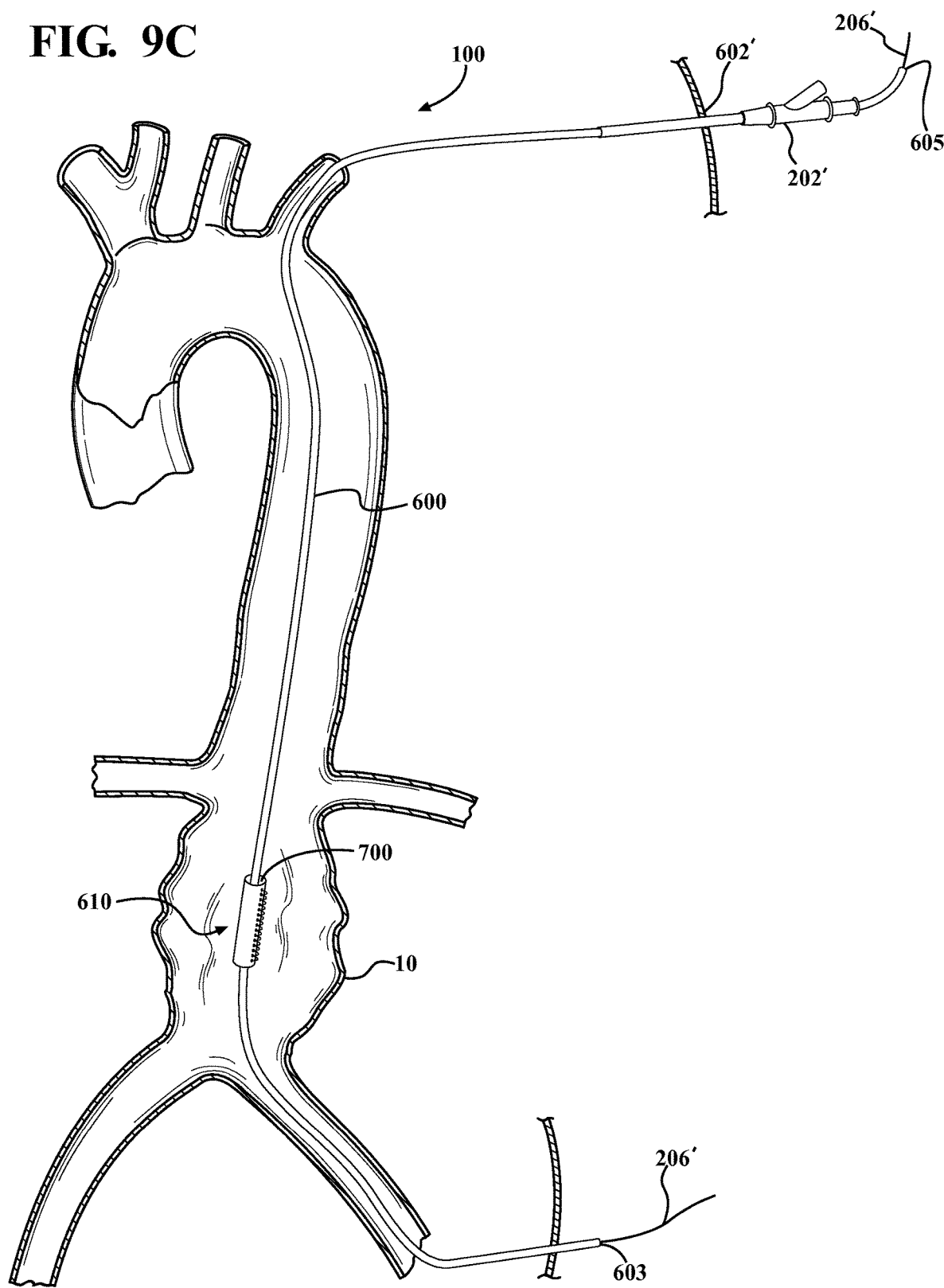
FIG. 9C shows a schematic representation of human anatomy with a first catheter protruding from a first access site and a second access site with a constrained device on the first catheter in situ.

Alternatively, a delivery system can include a catheter having an elongated first portion and an elongated second portion, wherein a constrained device is mounted to the catheter in a constrained or delivery configuration between the first portion and second portion. The elongated first and second portions can be integral to form the catheter. Alternatively, the elongated first and second portions can be separate and connectable or releasably connectable to form the catheter. For example, a catheter 600 is shown in FIG. 9A having a first portion 602 and a second portion 604. The first portion 602 is elongated, extends along a first longitudinal axis 606 thereof, and terminates at a first end 603 of the catheter 600. Similarly, the second portion 604 is elongated, extends along a second longitudinal axis 608 thereof, and terminates at a second end 605 of the catheter 600. An expandable device 700 is supported on a middle section 610 of the catheter 600 between the first portion 602 and second portion 604. The expandable device 700 can be radially constrained in a delivery configuration suitable for endoluminal delivery. The catheter 600 can be inserted into the vasculature, as described above in other embodiments, such that the first portion 602 extends outwardly from a first access site 102' via a first introducer sheath 202' and the second portion 604 extends outwardly from a second access site 104', optionally via a second introducer sheath 204'. The first and second portions 602, 604 extending outside of the body can be pushed, pulled and rotated to axially and rotatably position the expandable device 500 at the treatment site.

Alternatively, one of the elongated first and second portions of the catheter can have a smaller diameter than the other of the elongated first and second portions. For example, as shown in FIG. 9B, the second portion 604' of the catheter 600' can have a smaller diameter than the first portion 602' of the catheter 600'.

Alternatively, one of the elongated first and second portions of the catheter can be substantially more flexible than the other of the elongated first and second portions of the catheter.

Alternatively, one or both of the first and second portions of the catheter can have substantially no column strength or at least can be flexible so as to not be effectively pushable into and through the vasculature.

Alternatively, the first and second portions of the catheter can be axially compressible toward each other to cause the catheter and implant to buckle. This buckling, when combined with rotation of the catheter may be useful in correct and accurate placement of an endoluminal device.

Alternatively, one or both of the first and second portions of the catheter can be tapered toward the respective first and second ends to facilitate entry into and movement of the catheter through vasculature.

Alternatively, one of the first and second catheters may in the form of an ePTFE fiber, wherein the fiber may not have an inner lumen.

Referring to FIGS. 10-14, a delivery system is shown utilizing both trans-apical access and trans-femoral access sites, which allows push-pull positioning and delivery of an expandable implant inside of, at or near the heart through manipulation of at least two portions or members of the delivery system from outside of the body from the respective trans-apical and trans-femoral access sites.

Figure 10:
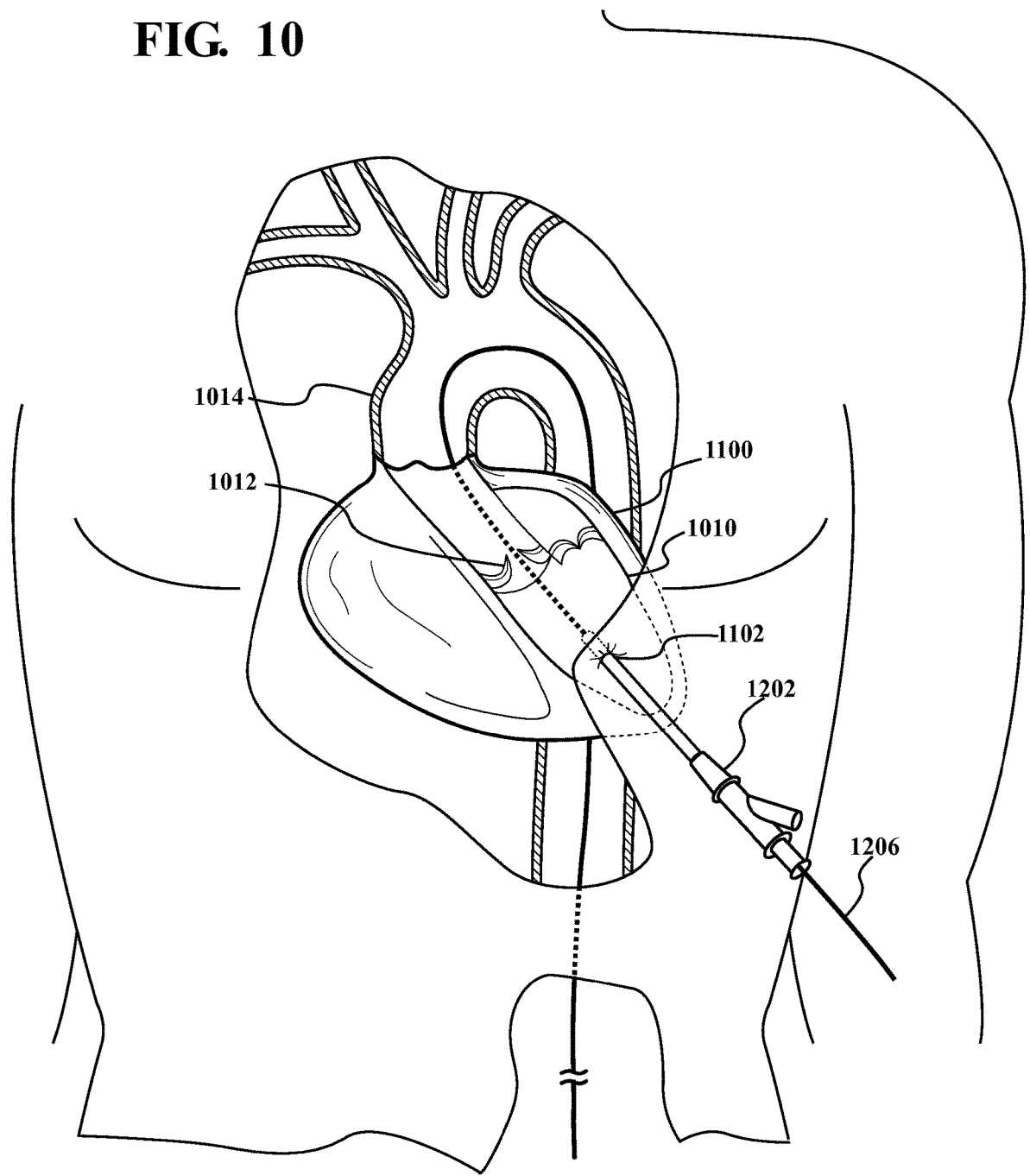
FIG. 10 shows a schematic of human anatomy with a guidewire fed from a first access site out a second access site.
Figure 11:
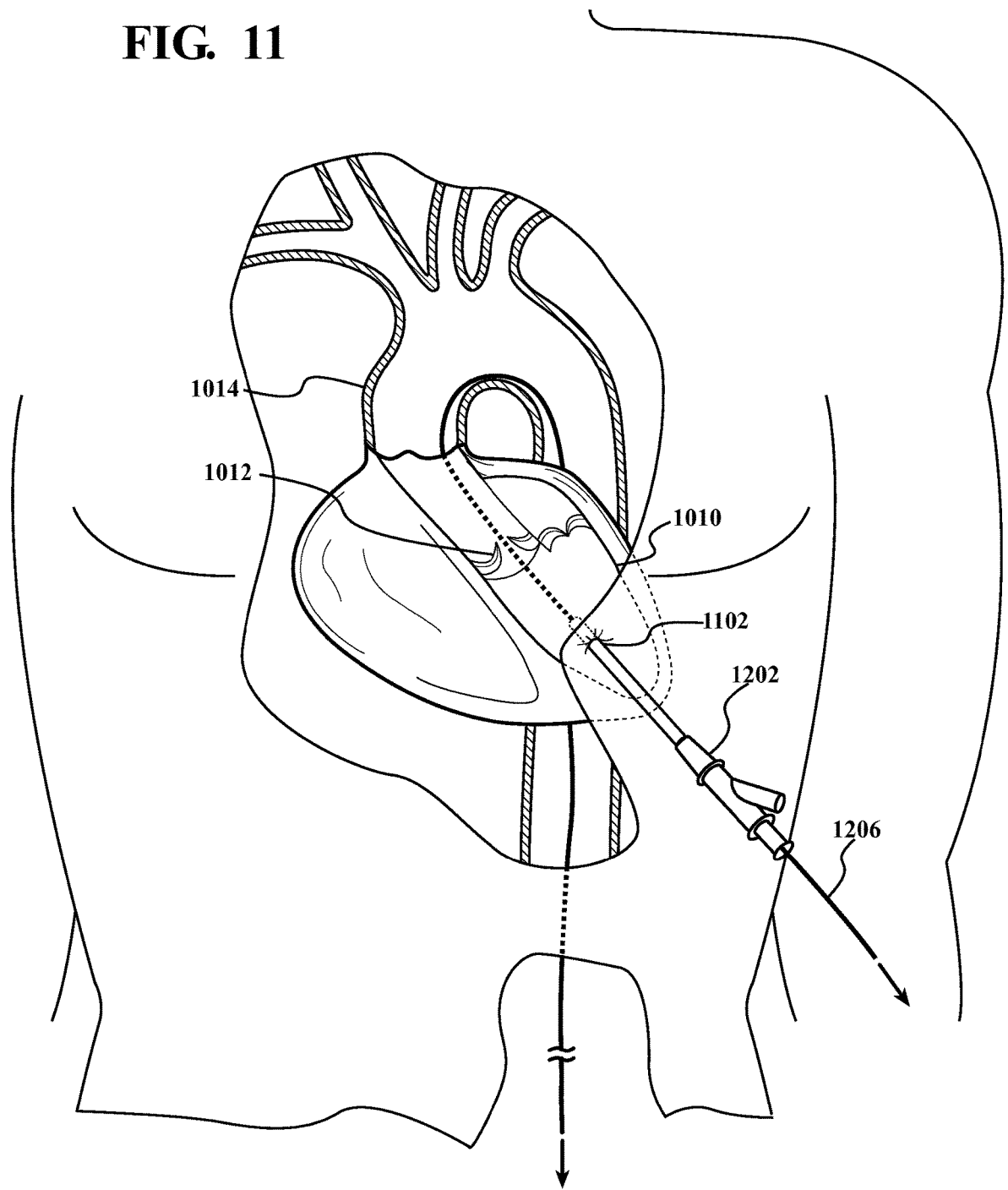
FIG. 11 shows a schematic of human anatomy with a guidewire fed from a first access site out a second access site and the guidewire able to be manipulated from the first access site and the second access site.

The delivery system can, for example, be used to deploy an endoprosthetic device, such as a stent graft for treating the ascending portion of the aortic arch or a valve device for replacing a failing valve. Continuing with these examples, a guidewire 1206 can be inserted through the trans-apical access site and into the left ventricle 1010 of the heart 1100, as shown in FIG. 10. The guidewire 1206 can be routed through the aortic valve 1012, the aorta 1014, a femoral artery of one of the legs, and out of the body via the trans-femoral access site (not shown), resulting in a "body floss" or "through-and-through" access configuration, wherein opposite terminal ends 1205, 1207 of the guidewire 1206 extend outside of the body from respective trans-apical and trans-femoral access sites 1102, 1104, as shown in FIG. 11. Optionally, the guidewire 1206 can be tensioned by pulling on the opposite ends 1205, 1207 of the guidewire 1206, as illustrated by the arrows "a" and "b" in FIG. 11, to cause the guidewire 1206 to extend along the inside radius of the aortic arch.

A first introducer sheath 1202 can be inserted over the guidewire 1206 and into the heart 1100 via the trans-apical access site to facilitate introduction of surgical implements therethrough during the procedure. Similarly, a second introducer sheath (not shown) can be inserted over the guidewire 1206 to facilitate femoral introduction of surgical implements through the trans-femoral access site.

Figure 12:
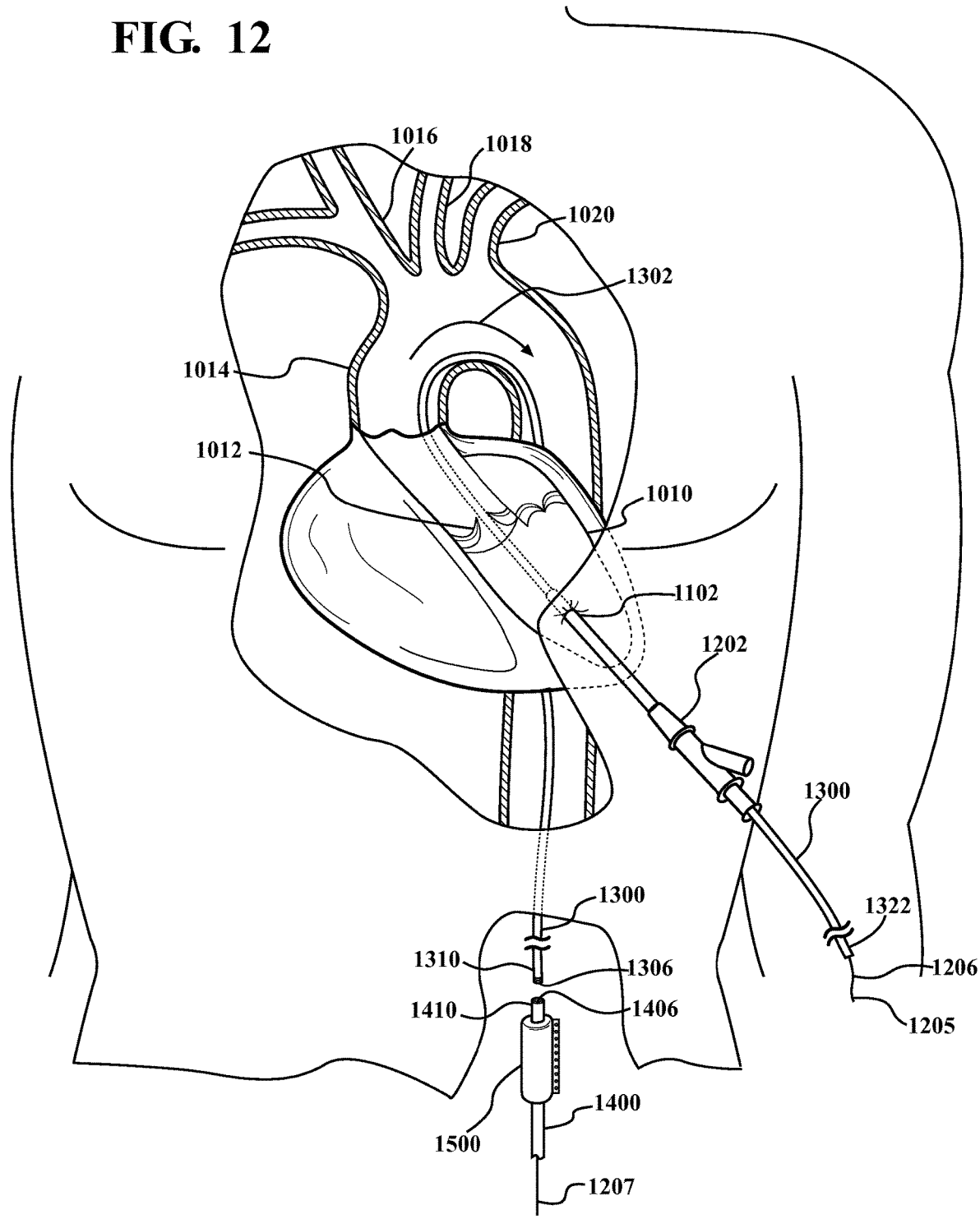
FIG. 12 shows a schematic of human anatomy with a first catheter fed through a first access site and through a second access site, and a second catheter with a device constrained along the second catheter able to be connected extracorporeal to the first catheter.
Figure 13:
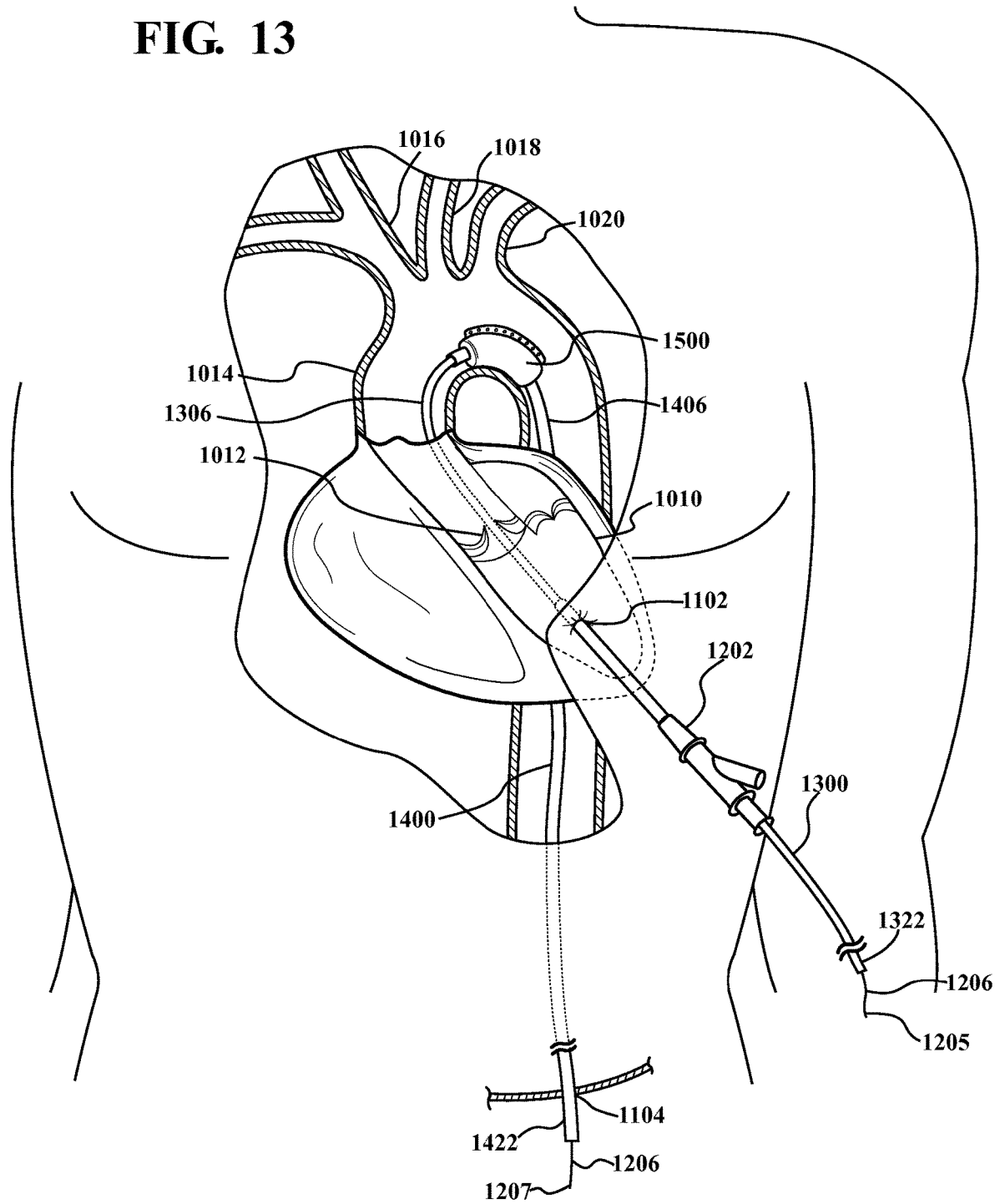
FIG. 13 shows a schematic of human anatomy with a first catheter protruding from a first access site and a second catheter protruding from a second access site and a device constrained along the second catheter and positioned at an implant site by the first catheter and second catheter.
Figure 14:
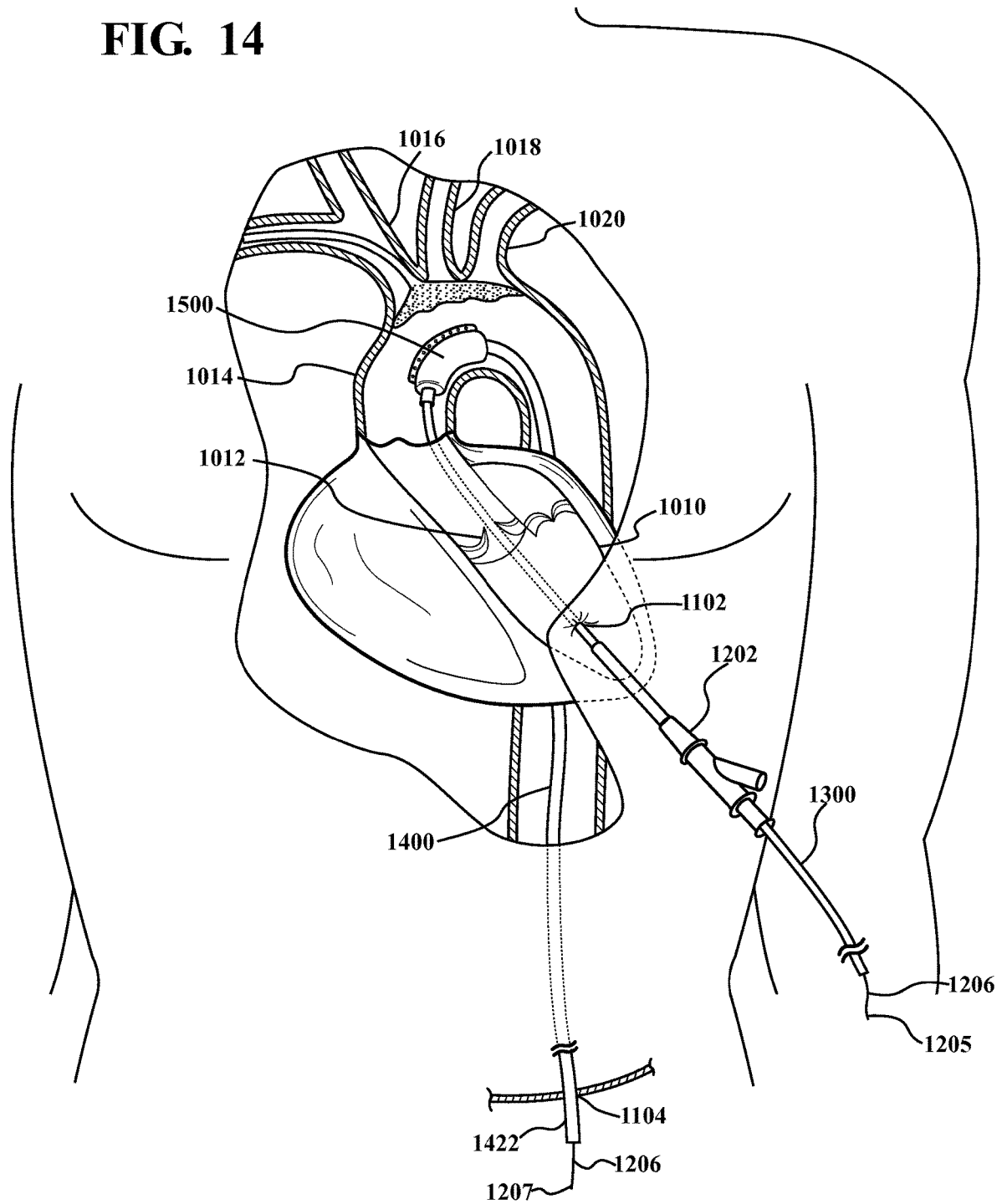
FIG. 14 shows a schematic of human anatomy with an embolic protection device and a catheter device positioned near the implant side, where the catheter device is manipulated into position via a first catheter connected to a second catheter.

Referring to FIG. 12, a first catheter, generally indicated at 1300, includes a leading end 1306 and an opposite trailing end 1322. The first catheter 1300 has a guidewire lumen 1310 through which the guidewire 1206 can be routed. A first end 1205 of the guidewire 1206 can be inserted into the guidewire lumen 1310 at the leading end 1306 of the first catheter 1300. The leading end 1306 of the first catheter 1300 can be fed into the vasculature through the trans-apical access site 1102 via the first introducer sheath 1202. The first catheter 1300 can then be pushed along the guidewire 1206 in the direction indicated at 1302 until the leading end 1306 exits the trans-femoral access site (not illustrated). The trailing end 1322 of the first catheter 1300 remains outside of the body and extends from the first access site 1102 via the first introducer sheath 1202. In this configuration, the catheter 1300 can be maneuvered by pushing or pulling the leading 1306 and trailing 1322 ends of the first catheter 1300 from outside of the body. Further, it should be noted that optionally tensioning the guidewire 1206, as illustrated in FIG. 11, can result in the first catheter 300, or any other implement delivered over the guidewire 1206, tracking and remaining along the inside radius of the aortic arch, as shown in FIGS. 12-14.

Still referring to FIG. 12, a second catheter, generally indicated at 1400, includes a leading end 1406 and an opposite trailing end 1422. The second catheter 1400 has a guidewire lumen 1410 for receiving the guidewire 1206 therethrough. The second end 1207 of the guidewire 1206 can be inserted into the guidewire lumen 1410 at the leading end 1406 of the second catheter 1400. The second catheter 1400 can be pushed along the guidewire 1206 until the leading ends 306, 306 engage.

An endoprosthetic device for treating a failing heart valve or disease along the ascending portion of the aorta or aortic arch can be releasably coupled to one of the first and second catheters at or near the leading end thereof. The endoprosthetic device can be releasably maintained or radially compressed toward a delivery configuration for endoluminal delivery by any suitable constraining means, such as a film constraining sleeve, a constraining tether or lattice, retractable sheath and the like. Optionally, one or more constraining means or combination of constraining means can be configured to allow staged expansion through one or more intermediate expanded states leading to full deployment. As shown in FIG. 12, for example, a device 1500 is releasably held in a delivery configuration coupled at or near the leading end 1406 of the second catheter 1400.

The leading ends 1306, 1406 of the first and second catheters 1300, 1400 can be configured for matingly engaging or coupling to each other. Further, the leading ends 1306, 1406 can be configured for releasably coupling to each other. The leading ends 1306, 1406 of the first and second catheters 1300, 1400 can be coupled to each other extra corpeal or in situ. Once the leading ends 1306, 1406 are coupled, the trailing ends 1322, 1422 of the first and second catheters 1300, 1400 can be accessed outside of the body from the respective trans-apical 1102 and trans-femoral 1202 access sites 1102, 1104 and pushed, pulled and rotated to axially and rotatably position the device 1500 at the treatment site, as shown in FIG. 13. After the device 1500 has been positioned at a desirable location and orientation at the treatment site, the device 1500 can be fully deployed to engage the surrounding tissues at the treatment site.

Other surgical tools may be delivered through a third access point to the aortic arch through one of the major branch arteries along the aortic arch in connection with the deployment of the device at or in the heart or along the aortic arch. As shown in FIG. 14, for example, a filter 1800 may be deployed to filter blood entering the branch arteries 1016, 1018, 1020.

It will be apparent to those skilled in the art that various modifications and variations can be made in the present present disclosure without departing from the spirit or scope of the present disclosure. Thus, it is intended that the present present disclosure cover the modifications and variations of this present disclosure provided they come within the scope of the appended claims and their equivalents.

What is claimed is:

1. A system for delivery of a medical device, said system comprising:
   a first member including an elongated first portion and a guidewire lumen, wherein the first member is configured to extend outside of a body from a first percutaneous access site;
   a second member separate from the first member and configured to be inserted into a body of a patient separately from the first member, the second member including an elongated second portion, wherein the second member is configured to extend outside the body from a second percutaneous access site, the second portion defining a a bore and the second percutaneous access site being different from the first percutaneous access site;
   a constraining member; and
   a medical device disposed about an exterior of the first portion of the first member and releasably retained in a delivery configuration about the first portion by the constraining member for endoluminal delivery of the medical device toward a treatment site in a human vessel,
   wherein the first and second members allow for positioning of the medical device at the treatment site by manipulation of the first portion and the second portion from outside of the body, and wherein the second portion is configured to receive the medical device and the constraining member within the bore of the second portion while the medical device is disposed about the first portion of the first member in the delivery configuration such that the second portion is releasably coupleable to the medical device, wherein an end of one of the first and second portions is configured to be received within an end of the other first and second end portions.

2. The system as set forth in claim 1, wherein the first portion of the first member and the second portion of the second member are separable so as to be axially displaceable relative to each other.

3. The system as set forth in claim 2, wherein the bore is defined in the second portion of the second member, wherein the second portion of the second member includes a generally annular inner wall defining the bore for receiving at least a first section of the medical device therein.

4. The system as set forth in claim 3, wherein the inner wall engages and maintains at least the first section of the medical device in the delivery configuration.

5. The system as set forth in claim 4, wherein at least the first section of the medical device can be deployed by axial displacement of the second portion of the second member relative to the medical device.

6. The system as set forth in claim 5, wherein the medical device is an expandable stent graft.

7. The system as set forth in claim 6, wherein the medical device is self-expanding.

8. The system as set forth in claim 7, wherein a second section of the medical device is releasably retained in the delivery configuration by the constraining member, wherein the constraining member is a flexible constraining sleeve.

9. The system as set forth in claim 8, wherein the second section of the medical device is mounted to the first portion of the first member.

10. The system as set forth in claim 3, wherein the first portion of the first member and the second portion of the second member are releasably coupled to each other.

11. The system as set forth in claim 10, wherein an engagement between the medical device and the inner wall of the second portion of the second member defines the releasable coupling between the first portion of the first member and the second portion of the second member.

12. The system as set forth in claim 1, wherein the constraining member is a flexible constraining sleeve.

13. The system as set forth in claim 12, wherein the first member includes a mounting portion between the first and second portions, the medical device being mounted to the mounting portion.

14. The system as set forth in claim 1, wherein at least one of the first portion of the first member and the second portion of the second member have substantially no column strength.

15. The delivery system as set forth in claim 14, wherein a compressive force to a tensile force ratio of the first portion is less than 1/8.

16. The delivery system as set forth in claim 14, wherein a compressive force ratio of the first portion to the second portion is less than 8/10.

17. A delivery system for an implantable prosthesis, said delivery system comprising:
   a first elongated delivery member including a first guidewire limen;
   a constraining member;
   a second elongated delivery member separate from the first elongated delivery member, and configured to be inserted into a body of a patient separately from the first elongated delivery member; and
   an expandable device coupled to the first and second elongated delivery members and constrained by the constraining member, wherein a partial deployment of a portion of the expandable device within a bore of the second delivery member and toward engagement with the second delivery member while the expandable device is disposed about an exterior of the first delivery member defines a releasable coupling between the expandable device and the second delivery member, wherein the partial deployment includes releasing the constraining member from the portion of the expandable device, wherein an end of one of the first and second elongated delivery members is configured to be received within an end of the other first and second elongated delivery members.

18. The delivery system as set forth in claim 17, wherein the second delivery member includes an annular surface defining the bore.

19. The delivery system of claim 18, wherein the expandable device is partially deployed and engaged with the annular surface thereby defining the releasable coupling.

20. The system of claim 17, wherein each of the elongated first portion and the elongated second portion is at least 3× the length of the expandable device.

21. A system for delivery of a medical device, said system comprising:
   a catheter having a mounting portion; and
   a medical device disposed about an exterior of the mounting portion and constrained by a constraining member,
   wherein the catheter further includes an elongated first portion having a first guidewire lumen and configured to exit a body through a first insertion site and an elongated second portion configured to exit the body through a second insertion site that is different from the first insertion site while the medical device is positioned at the treatment site, the second portion being configured to receive the medical device and the constraining member within a bore of the second portion while the medical device is disposed about the mounting portion, and
   wherein at least one of the first and second portions has substantially no column strength, wherein an end of one of the first and second portions is configured to be received within an end of the other first and second end portions.

22. A system for delivery of a medical device, said system comprising:
   a first elongated delivery member having a first guidewire lumen and configured to exit a body through a first insertion site;
   a second elongated delivery member configured to exit the body through a second insertion site that is different from the first insertion site, the second elongated delivery member being separate from the first elongated delivery member and configured to be inserted into a body of a patient separately from the first elongated delivery member; and
   a medical device mounted between the first elongated delivery member and the second elongated delivery member such that the medical device is disposed about an exterior of the first elongated delivery member and constrained by a constraining member such that the medical device, the first elongated delivery member, and the constraining member are disposed within a bore of the second elongated delivery member,
   wherein the first and second elongated delivery members extending outside the body through the respective first and second insertion sites are configured to be manipulated to position the medical device, and
   wherein at least one of the first elongated delivery member and the second elongated delivery member is sufficiently flexible in that it is not capable of being advanced through the body by pushing, wherein an end of one of the first and second elongated delivery members is configured to be received within an end of the other first and second elongated delivery members.

23. The system as set forth in claim 22, wherein both the first elongated delivery member and the second elongated delivery member are sufficiently flexible in that they are not capable of being advanced through the body by pushing.

24. The system of claim 22, wherein each of the first elongated delivery member and the second elongated delivery member is at least 3× the length of the medical device; and wherein at least one of the first elongated delivery member and the second elongated delivery member is sufficiently flexible in that it is not capable of being advanced through the body by pushing.

25. The system as set forth in claim 24, wherein both the first elongated delivery member and the second elongated delivery member are sufficiently flexible that they are not capable of being advanced through the body by pushing.

26. A delivery system for an implantable prosthesis, said delivery system comprising:

an expandable implantable prosthesis;

a first catheter having a first guidewire lumen, a first catheter outer wall, and a first catheter inner wall, the first catheter being configured to extend outside of a body from a first percutaneous access site; and a second catheter having a second catheter outer wall and a second catheter inner wall, the second catheter being configured to extend outside of the body from a second percutaneous access site that is different from the first percutaneous access site, the second catheter being separate from the first catheter and configured to be inserted into a body of a patient separately from the first catheter, wherein the first catheter inner wall extends along the second catheter outer wall such that the first and second catheters partially overlap, and wherein the expandable implantable prosthesis is constrained at least partially by the first catheter inner wall and constrained at least partially along the second catheter outer wall by a releasable constraining member, wherein an end of one of the first and second catheters is configured to be received within an end of the other first and second catheters.

27. The delivery system as set forth in claim 26, wherein the constraining member releasably constraining the implantable prosthesis along the second catheter outer wall is a sheath.

28. The delivery system as set forth in claim 27, wherein the second catheter outer wall and the second catheter inner wall are substantially parallel.

29. The delivery system as set forth in claim 28, wherein the first catheter inner wall is textured.

30. The delivery system as set forth in claim 29, wherein the constraining member is an ePTFE tubular structure.

31. A system for delivery of a medical device, said system comprising:

a delivery member including an elongated first portion having a first guidewire lumen and configured to extend outside of a body from a first percutaneous access site, and an elongated second portion configured to extend outside the body from a second percutaneous access site that is different from the first percutaneous access site, the elongated second portion being separate from the elongated first portion and configured to be inserted into a body of a patient separately from the elongated first portion; and a medical device releasably coupled to the delivery member and releasably retained in a delivery configuration by a constraining member for endoluminal delivery of the medical device toward a treatment site in a human vessel, wherein the delivery member allows for positioning of the medical device at the treatment site by manipulation of the first portion and the second portion from outside of the body, and wherein the second portion is releasably coupleable with the first portion such that the first and second portions are coaxially aligned with the medical device, the constraining member, wherein an end of one of the first and second portions is configured to be received within an end of the other first and second end portions.

* * * * *